United States Patent
Melder et al.

(10) Patent No.: US 12,150,717 B2
(45) Date of Patent: Nov. 26, 2024

(54) TRACKING DEVICE, SURGICAL INSTRUMENT INCLUDING SAME, AND SURGICAL NAVIGATION SYSTEM WITH THE SURGICAL INSTRUMENT

(71) Applicant: Stryker European Operations Limited, Carrigtwohill (IE)

(72) Inventors: Ulrich Melder, Rust (DE); Maxi Frei, Freiburg (DE)

(73) Assignee: Stryker European Operations Limited, Carrigtwohill (IE)

( * ) Notice: Subject to any disclaimer, the term of this patent is extended or adjusted under 35 U.S.C. 154(b) by 833 days.

(21) Appl. No.: 17/313,062

(22) Filed: May 6, 2021

(65) Prior Publication Data
US 2021/0353364 A1    Nov. 18, 2021

(30) Foreign Application Priority Data

May 14, 2020 (EP) .................................... 20174670

(51) Int. Cl.
*A61B 34/20* (2016.01)

(52) U.S. Cl.
CPC ...... *A61B 34/20* (2016.02); *A61B 2034/2051* (2016.02)

(58) Field of Classification Search
CPC ............ A61B 34/20; A61B 2034/2051; H02G 15/007
See application file for complete search history.

(56) References Cited

U.S. PATENT DOCUMENTS

| | | | |
|---|---|---|---|
| 7,420,122 B2 * | 9/2008 | King, Jr. ................ | H01R 13/59 174/87 |
| 9,656,042 B2 * | 5/2017 | Takagi ............. | A61M 25/0097 |
| 2014/0159707 A1 | 6/2014 | Ashe | |
| 2017/0119473 A1 | 5/2017 | Clopp | |
| 2020/0038115 A1 | 2/2020 | Schwamb et al. | |

FOREIGN PATENT DOCUMENTS

| | | |
|---|---|---|
| CN | 102985128 A | 3/2013 |
| WO | 2017127722 A1 | 7/2017 |

OTHER PUBLICATIONS

English language abstract for CN 102985128 A extracted from espacenet.com database on Dec. 11, 2023, 1 page.

* cited by examiner

*Primary Examiner* — Joel Lamprecht
(74) *Attorney, Agent, or Firm* — Howard & Howard Attorneys PLLC

(57) ABSTRACT

A tracking device for use in a surgical navigation system. The device includes an electromagnetic sensor configured to generate a sensor signal that depends on an external electromagnetic field. The device also includes at least one line element electrically connected to the sensor. The line element includes a first line section, a second line section, and a third line section arranged between the first and second line sections. A strain relief unit includes a core, an outer surface, and at least one recess which extends in the outer surface circumferentially around a longitudinal axis of the core. The first line section extends into the strain relief unit on a first side of the strain relief unit, the second line section extends into the strain relief unit on a second side of the strain relief unit opposite the first side, and the third line section extends within the recess.

20 Claims, 7 Drawing Sheets

TRACKING DEVICE, SURGICAL INSTRUMENT INCLUDING SAME, AND SURGICAL NAVIGATION SYSTEM WITH THE SURGICAL INSTRUMENT

PRIORITY CLAIM

This application claims priority under 35 U.S.C. § 119 to European Patent Application No. 20174670.8, filed May 14, 2020, the entire contents of which are hereby incorporated by reference.

TECHNICAL FIELD

This disclosure relates to a tracking device, in particular to an electromagnetic tracking device suitable for use in surgical navigation. The disclosure also relates to a surgical instrument comprising the tracking device, and to a surgical navigation system comprising the surgical instrument.

BACKGROUND

Surgical navigation systems of different types are known. Such systems are commonly used for tracking a position of a surgical instrument, for example relative to a patient. During a surgical procedure, the surgical instrument may be used partly within the body of a patient. In many cases, in particular the parts of the surgical instrument that are located within the patient's body cannot be observed easily by the surgeon. Using a tracking device which defines at least one specific position of the surgical instrument allows conclusions regarding the position of the surgical instrument with respect to the patient and possibly also conclusions regarding its orientation.

One known tracking method involves the use of an artificially generated external electromagnetic field. Knowing the properties of such an electromagnetic field allows for tracking a position using an electromagnetic sensor. The current induced in a coil depends on its movement as well as its orientation with respect to field lines of an external electromagnetic field in which the coil is positioned. Therefore, one or more coils are often used as electromagnetic sensors in electromagnetic surgical navigation systems.

In some cases, the electromagnetic sensor is placed at a tip of the surgical instrument, such as at the tip of a stylet. A surgical instrument of this type is known for instance from US 2020/0038115 A1. Electrical wiring including electrical lines typically extend from the electromagnetic sensor at the tip of the surgical instrument along a tool head of the surgical instrument to a base portion such as a handle, from where it further extends out of the surgical instrument and connects the electromagnetic sensor to a control computer. As in many cases of moving corded instruments, an axial strain relief of some sort is often provided to prevent pulling forces from acting onto and potentially damaging the electromagnetic sensors.

A twist-on strain relief wire connector is known from U.S. Pat. No. 7,420,122 B2, which connector defines an internal space for receiving a coil and comprises a deformable insert with a central wire passageway through which a line element extends into the internal space and out of the internal space in order to allow electrical connection to the coil.

In surgical instruments such as the one known from US 2020/0038115 A1, a strain relief can be implemented by winding a fixation member such as an insulation wrapping around a base element, wherein windings of the fixation member overlap an electric line. When a pulling force is exerted onto the electric line, the windings tighten and act as a strain relief.

SUMMARY

There is a need for a reliable strain relief mechanism for an electric line element that connects to an electromagnetic sensor of a tracking device. It is therefore an object to provide such a strain relief mechanism.

A tracking device for use in a surgical navigation system is disclosed. According to one aspect, the tracking device comprises an electromagnetic sensor configured to generate a sensor signal that depends on an external electromagnetic field. Furthermore, the tracking device comprises at least one line element electrically connected to the electromagnetic sensor, wherein the line element comprises a first line section, a second line section, and a third line section arranged between the first line section and the second line section. In addition, the tracking device comprises a strain relief unit comprising a core, wherein the core comprises a longitudinal axis, an outer surface and at least one recess which extends in the outer surface circumferentially around the longitudinal axis, wherein the first line section extends into the strain relief unit on a first side of the strain relief unit, the second line section extends into the strain relief unit on a second side of the strain relief unit, in particular opposite the first side, and the third line section extends within the recess.

According to a second aspect, a surgical instrument is provided which comprises a tracking device according to this disclosure.

According to a third aspect, a surgical navigation system for tracking a position of a surgical instrument is provided. The surgical navigation system comprises a surgical instrument according to this disclosure. Furthermore, the surgical navigation system comprises a field generator for generating an electromagnetic field and a localizer connected to the electromagnetic sensor of the tracking device of the surgical instrument for determining a position of the surgical instrument based on a sensor signal received from the electromagnetic sensor.

The electromagnetic sensor may be an electromagnetic position sensor. The electromagnetic sensor may comprise at least one coil. In some embodiments, the electromagnetic sensor is a coil. The electromagnetic sensor may comprise a combination of two coils that are arranged angularly offset to each other. The sensor signal may be a digital signal. In some embodiments, the sensor signal is an analog signal. The sensor signal may be at least one of a current and a voltage signal. The sensor signal may depend on a current and/or voltage induced in the coil. In particular, the sensor signal may be the current and/or voltage induced in the coil.

The localizer of the surgical navigation system may comprise a current sensor and/or a voltage sensor for analyzing and/or receiving the sensor signal received from the electromagnetic sensor. The localizer may comprise a processing unit configured to execute a computer program for determining a position and/or orientation of the tracking device and/or the surgical instrument depending on the sensor signal received from the electromagnetic sensor and in some instances further depending on at least one property of the field generator and/or the generated electromagnetic field.

The line element may be an electrical line element. In particular, the line element may be part of an electric wiring. For instance, the line element may comprise at least one cable. In some embodiments, the line element comprises a twisted pair cable. The line element may be integrally formed with the electromagnetic sensor. In particular, the electromagnetic sensor may comprise a coil line element wound to a coil, wherein the coil line element may be part of a cable, and wherein said cable may comprise two connection sections connected to the coil line element which are twisted to form a twisted pair cable that is part of the line element. In case of an electromagnetic sensor with two coils, two twisted pair cables may be present. The line element may comprise a wire insulation.

The recess may comprise at least one groove formed in the outer surface of the core. The recess may comprise a depth that is equal to or greater than the diameter of the third line section. In some embodiments, the third line section is arranged inside the recess such that it does not intersect an envelope surface of the core that is defined by the outer surface in hypothetical absence of the recess.

The line element may extend through the strain relief unit such that the recess is configured to at least partly receive a strain force exerted onto to first line section with respect to the second line section.

In some embodiments, the recess extends around the core several times. The recess may describe several loops around the core. In some cases, the recess extends along a circle when viewed along the longitudinal axis. The recess may describe at least one closed circle when viewed along the longitudinal axis.

The recess may comprise at least two adjacent grooves, in particular two adjacent ring grooves, that extend around the core in a direction perpendicular to the longitudinal axis of the core. The at least to adjacent grooves may be arranged at adjacent positions along the longitudinal axis. The at least two adjacent grooves may extend circumferentially around the longitudinal axis in the outer surface of the core. The at least two adjacent grooves may be connected by a groove, in particular by a groove that extends parallel to the longitudinal axis.

The recess may be part of a thread formed in the outer surface of the core. The recess may describe a helical path around the core. The thread may comprise at least two different pitches. For instance, the pitch of the thread may be smaller or greater in a section of the thread in which the third line section is located than in a section of the thread in which the third line section is not located. In some embodiments, the third line section is located in a section of the thread which is located closest to the electromagnetic sensor and/or which is located closer to the electromagnetic sensor than a section of the thread in which the third line section is not located.

In some embodiments, the strain relief unit guides the line element in a guiding direction, wherein the guiding direction is at least one of a radially inward direction and a radially outward direction with respect to the longitudinal axis. With respect to the longitudinal axis, the first line section may be arranged at a first radial position and/or the second line section may be arranged at a second radial position, and the third line section may be arranged at a third radial position, wherein the first radial position and/or the second radial position may be radially inward of the third radial position when viewed along the longitudinal axis. The first line section and the second line section may be arranged coaxially with respect to each other. The first line section and/or the second line section may be arranged coaxially with respect to the longitudinal axis of the core.

In some cases, the line element comprises at least one of a line section arranged between the first line section and the third line section and a line section arranged between the second line section and the third line section, wherein said line section extends radially outward with respect to the longitudinal axis when viewed along the longitudinal axis. The line element may define a step shape when viewed in a direction perpendicular to the longitudinal axis. In some embodiments, the line element may define a double step shape, in particular a step up and a step down with respect to the longitudinal axis, when view in a direction perpendicular to the longitudinal axis.

In some embodiments, at least one opening is formed in the outer surface of the core, wherein the line element extends through the opening. In some embodiments, the core may comprise a hollow section comprising an internal space. The opening may connect an exterior of the core with the internal space.

The at least one opening may comprise at least one slit, wherein the slit is formed in the core, extends along the longitudinal axis of the core and overlaps the recess in an overlap region, wherein the at least one recess comprises one or more turns relative to the longitudinal axis, and wherein in the overlap region each turn of the recess around the core is interrupted by the slit. The slit may comprise a constant width when view along the longitudinal axis. In some embodiments, the slit comprises a first diameter in a radially outward section of the slit and a second diameter in a radially inward section of the slit, wherein the first diameter may be smaller than the second diameter. The slit may allow access through the outer surface of the core to the internal space. The first line section may extend substantially parallel to the longitudinal axis inside the internal space. The fourth line section may extend out of the internal space and through the slit.

The slit may comprise a base. The first line section may extend at the base of the slit. In some embodiments, the core may comprise a solid section in which the slit is formed, wherein the slit may have a depth that exceeds a diameter of the core.

In some embodiments, the strain relief unit further comprises a sleeve, wherein the core is arranged at least partly inside the sleeve. The sleeve may tightly fit over a section of the core. The sleeve and the core together may form the strain relief unit.

The core may be threaded into the sleeve. Additionally or alternatively, the core may be glued to the sleeve. In some embodiments, the core is glued to the sleeve such that the line element is not glued to the core and/or the sleeve. The third line section may be loose with respect to the core. In particular, the third line section may be not fixated stationarily to the core.

In some embodiments, the core comprises a cylindrical basic shape. The cylindrical basic shape may be the shape of the envelope surface. The sleeve may comprise a cylindrical basic shape. At least a section of the sleeve may be formed as hollow cylinder, wherein an inner diameter of said hollow cylinder may substantially equal an outer diameter of a section of the core configured for being covered by the sleeve.

The core may be a one-piece unit. Specifically, the core may be a monolithic structure. The core may for instance be a single plastic piece. In other embodiments, the core may comprise different separate parts that are connected, for instance by gluing, welding, clamping, press-fitting and/or by means of connecting elements.

In some embodiments, the tracking device may be part of a tracking module. The tracking module may be configured for being connected, in particular removably connected, to a surgical instrument.

The surgical instrument may comprise a surgical tool head with a first end, in particular a distal end, and a second end, in particular a proximal end, wherein the electromagnetic sensor is arranged at the first end, the strain relief unit is arranged at the second end, and the electric line element extends along the surgical tool head. The surgical head may further comprise a handle connected to the second end. The strain relief unit may be arranged at the second end. The strain relief unit may be arranged within the handle. In some embodiments, the surgical instrument comprises a connector that connects the surgical tool head to the handle. The connector may be a releasable connector, for instance for using the handle in a modular system, in particular optionally with different surgical tool heads. In some embodiments, the strain relief unit may be arranged within the connector. The first line section may extend through the handle towards the strain relief unit. The second line section may extend from the strain relief unit to the electromagnetic sensor, in particular along the surgical tool head.

The surgical tool head may be a stylet. The surgical instrument may be configured for being used in neurosurgery, for instance for navigated placement of shunts or ventricular catheters, in particular inside a patient's head.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
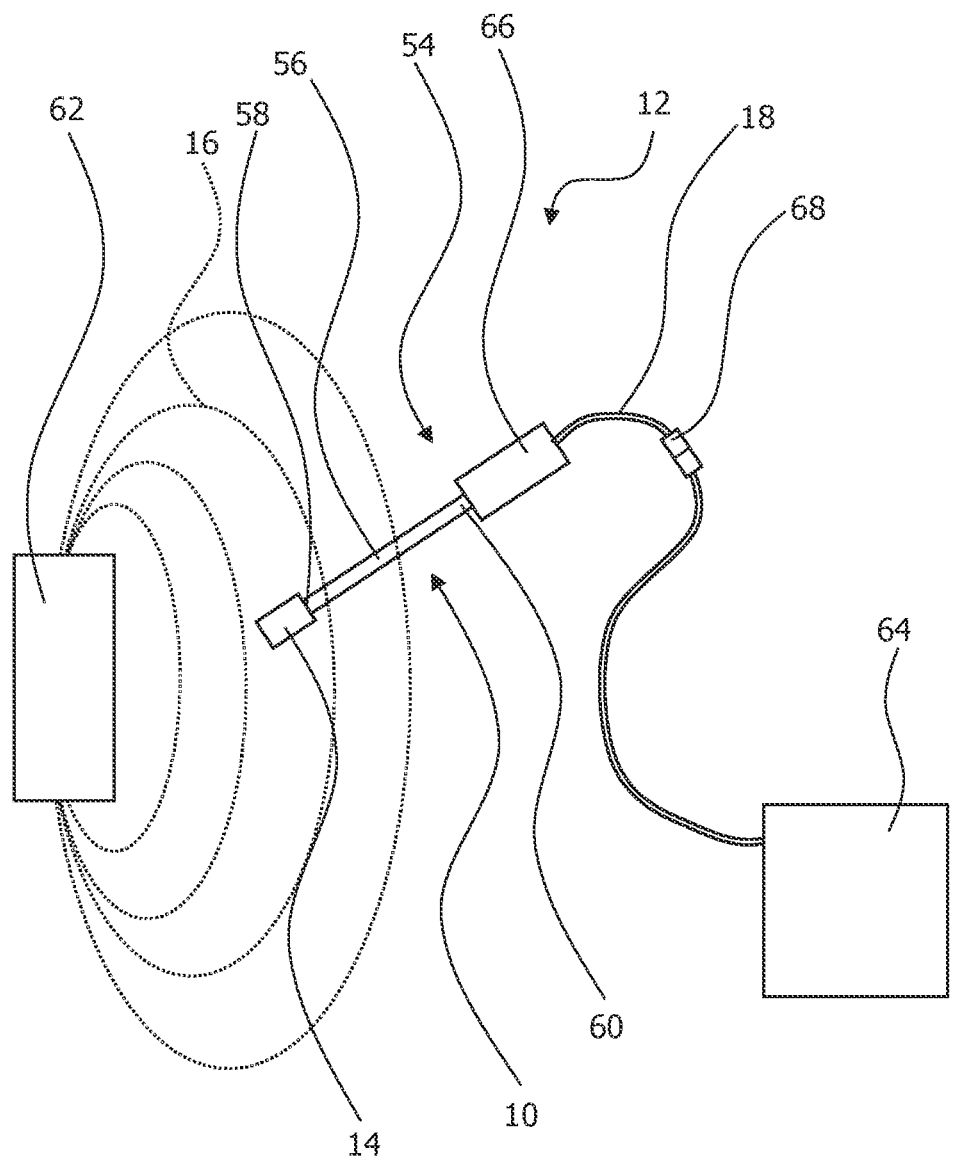
FIG. 1 shows a schematic view of a surgical navigation system with a surgical instrument.

In the following description, exemplary embodiments of a tracking device, a surgical instrument and a surgical navigation system will be explained with reference to the drawings. The same reference numerals will be used to denote the same or similar structural features.

FIG. 1 shows a schematic view of a surgical navigation system 12 with a surgical instrument 54 according to an embodiment of this disclosure. The surgical navigation system 12 comprises a field generator 62 for generating an external electromagnetic field 16, which is represented by a number of exemplary field lines. During navigation, for instance during a surgical procedure, a patient (not shown) is located within the external electromagnetic field 16. Hence, the surgical instrument 54 is moved within the external electromagnetic field 16 when being applied to the patient.

The surgical instrument 54 comprises a handle 66 and a surgical tool head 56. In the shown embodiment, the surgical tool head 56 is a stylet. The surgical tool head 56 comprises a first end 58 which is a distal end and a second end 60 which is a proximal end. An electromagnetic sensor 14 is arranged at the first end 58. The electromagnetic sensor 14 is part of a tracking device 10 which will be described below with reference to FIGS. 2 to 5.

Furthermore, the surgical navigation system 12 comprises a localizer 64 connected to the electromagnetic sensor 14 for determining a position of the surgical instrument 54 based on a sensor signal received from the electromagnetic sensor 14. The tracking device 10 comprises a line element 18 which extends through the handle 66 and the surgical tool head 56, thus connecting the electromagnetic sensor 14 to a connector 68. The connector 68 is removably connected to the localizer 64. In the shown embodiment, the localizer 64 may therefore be used with different types of surgical instruments 54.

The electromagnetic sensor 14 may comprise a coil and/or may be a coil. The external electromagnetic field 16 may be a constant electromagnetic field or a time-varying electromagnetic field, for example depending upon an operation mode of the surgical navigation system 12. The electromagnetic sensor 14 is configured to generate a sensor signal that depends on the external electromagnetic field 16. In the shown embodiment, the sensor signal is an analog signal, in particular an induced current and/or an induced voltage. Movement of the electromagnetic sensor 14 and/or the time variation of the external electromagnetic field 16 induces different currents and/or voltages in the electromagnetic sensor 14 leading to different sensor signals.

In other embodiments, the electromagnetic sensor 14 may comprise a processing unit for generating a digital sensor signal based on the detected external electromagnetic field 16. The line element 18 may then be used for transmitting said digital sensor signal.

The localizer 64 comprises a processing unit which is configured to determine a current position of the electromagnetic sensor 14 within the external electromagnetic field 16 depending on the sensor signal and at least one parameter describing the external electromagnetic field 16, such as a field strength, a field gradient, a time evolution of the field etc.

In the present exemplary embodiment, the line element 18 is a twisted pair cable. Both cables of the cable pair may be connected to opposite contacts of the electromagnetic sensor 14 (e.g., to the two ends of a coil thereof).

Figure 2:
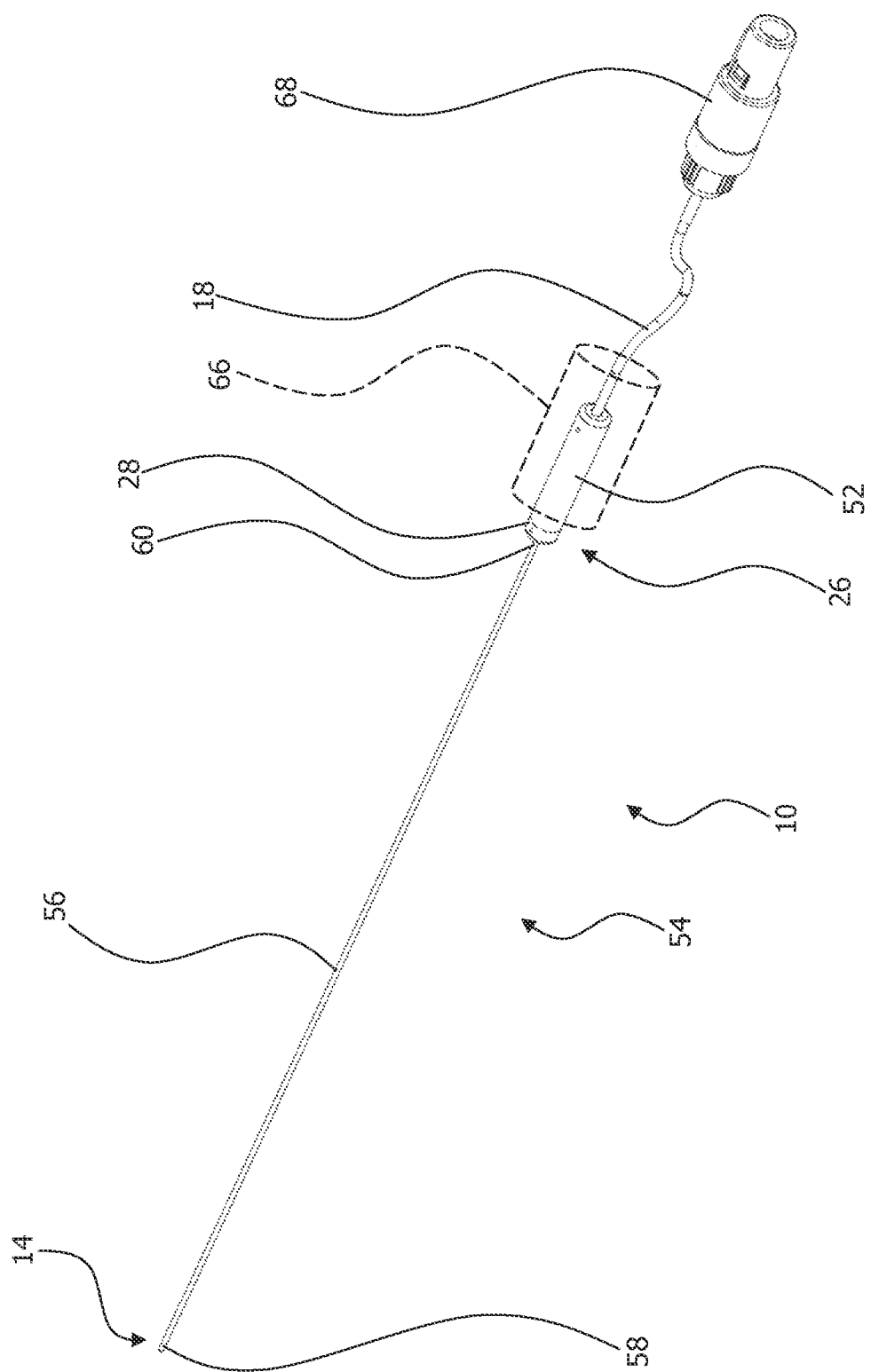
FIG. 2 shows a schematic perspective view of a part of the surgical instrument with a tracking device according to a first embodiment.
Figure 3:
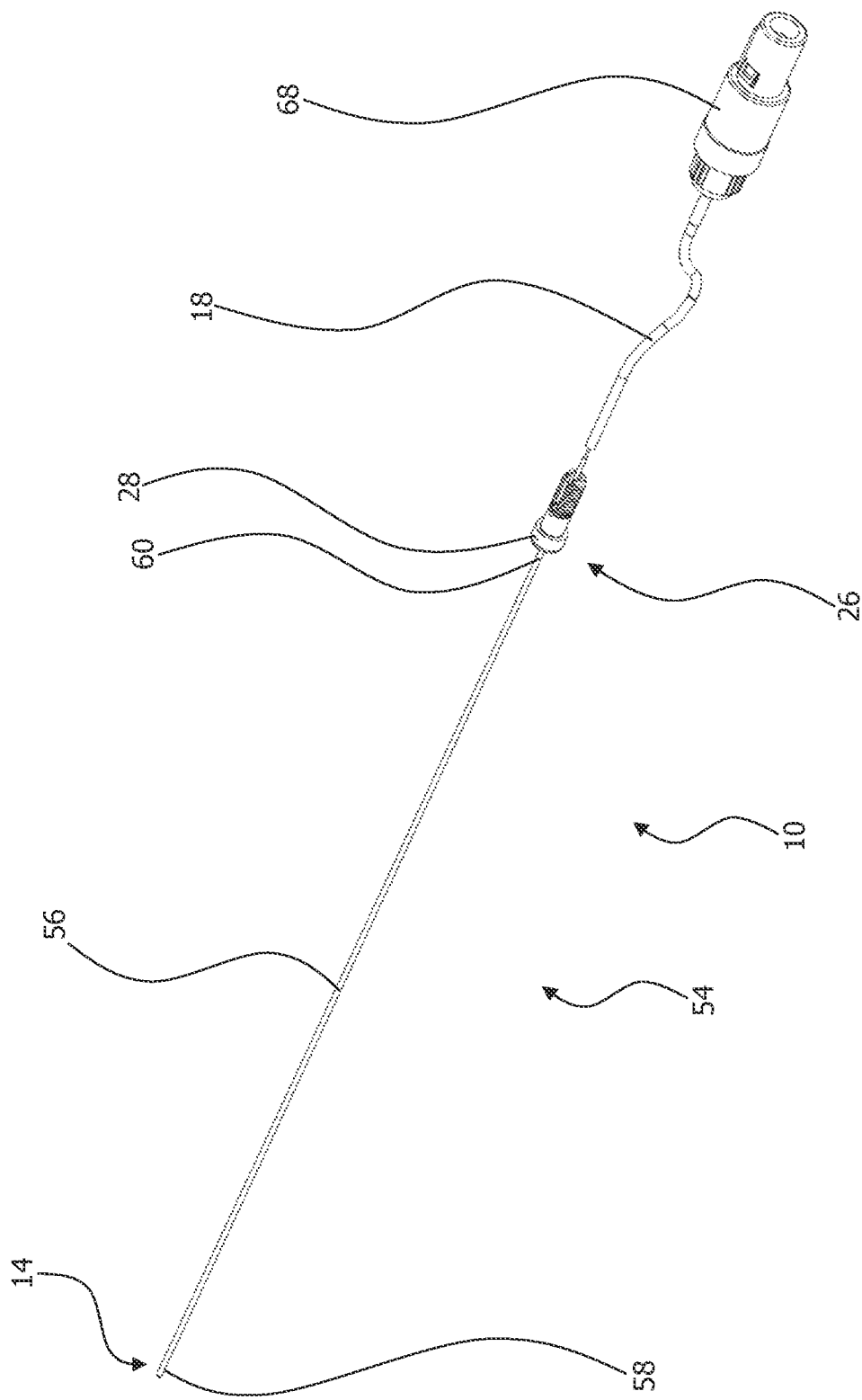
FIG. 3 shows a schematic perspective view of an interior of a part of the surgical instrument including a strain relief unit of the tracking device.

FIG. 2 shows a schematic perspective view of a part of the surgical instrument 54 with the tracking device 10. FIG. 3 shows a schematic perspective view of an interior of a part of the surgical instrument 54 including a strain relief unit 26 of the tracking device 10. The strain relief unit 26 is configured for providing a strain relief for the line element 18 and will be described below in greater detail. The strain relief unit 26 comprises a core 28 and a sleeve 52 fitted over the core 28.

In this embodiment, the connector 68 is implemented as releasable quick connector which allows for tool-free connection to and de-connection from the localizer 64. In other embodiments, there may be no connector 68, but the line element 18 may instead be directly connected to the localizer 64.

Figure 4:
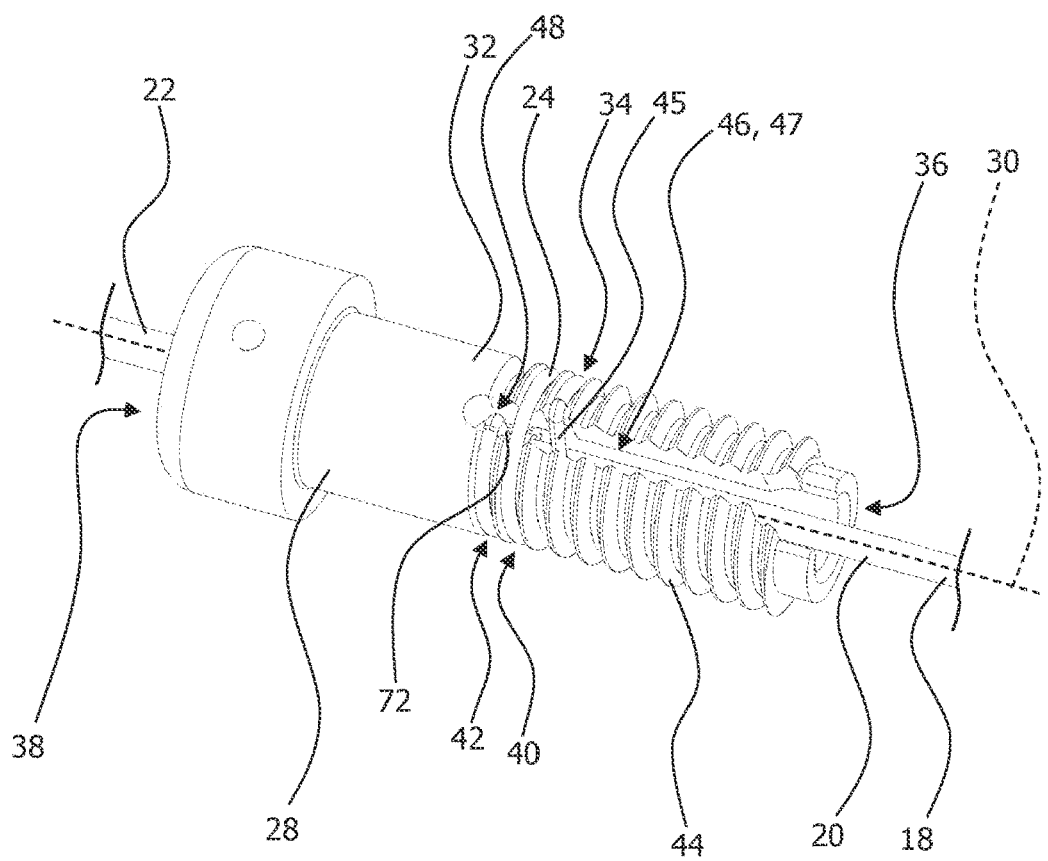
FIG. 4 shows a schematic perspective view of a core of the strain relief unit.

FIG. 4 shows a schematic perspective view of the core 28 of the strain relief unit 26. The core 28 comprises a longitudinal axis 30. Furthermore, the core 28 comprises an outer surface 32 and a recess 34 which extends in the outer surface 32 circumferentially around the longitudinal axis 30.

The core 28 may at least partly be made of plastic. In some embodiments, a core may at least partly be made of metal. In some embodiments, a core may at least partly be made of ceramics. Furthermore, a combination of different materials, in particular of the mentioned materials, may be used. The recess 34 extends around the core 28 several times. When viewed along the longitudinal axis 30, the recess 34 extends along a circle.

The recess 34 is part of a thread 44 formed in the outer surface 32 of the core 28. The recess 34 is arranged on a distal side of the thread 44. The recess 34 thus describes a helical path around the outer surface 32 of the core 28. The recess 34 is a helical groove.

The line element 18 comprises a first line section 20 which extends into the strain relief unit 26 from a first side. In the shown embodiment, the first side is a proximal side of the strain relief unit 26, in particular with respect to the connector 68 and/or the localizer 64. In addition, the line element 18 comprises a second line section 22 which extends into the strain relief unit 26 from a second side opposite the first side. In the shown embodiment, the second side is a distal side of the strain relief unit 26, in particular with respect to the connector 68 and/or the localizer 64.

The line element 18 further comprises a third line section 24 arranged between the first line section 20 and the second line section 22. The third line section 24 extends within the recess 34. The third line section 24 follows the helical path described by the recess 36. The third line section 24 is arranged within the thread 44.

The recess 34 has a V-shaped or a U-shaped cross-section, suitable for receiving the third line section 24. The recess 34 has a depth which assures that the third line section 24 is at least flush with the outer surface 32 of the core 28, i.e., the third line section 24 is flush with the outer surface 32 or recessed with respect to the outer surface 32.

Figure 5:
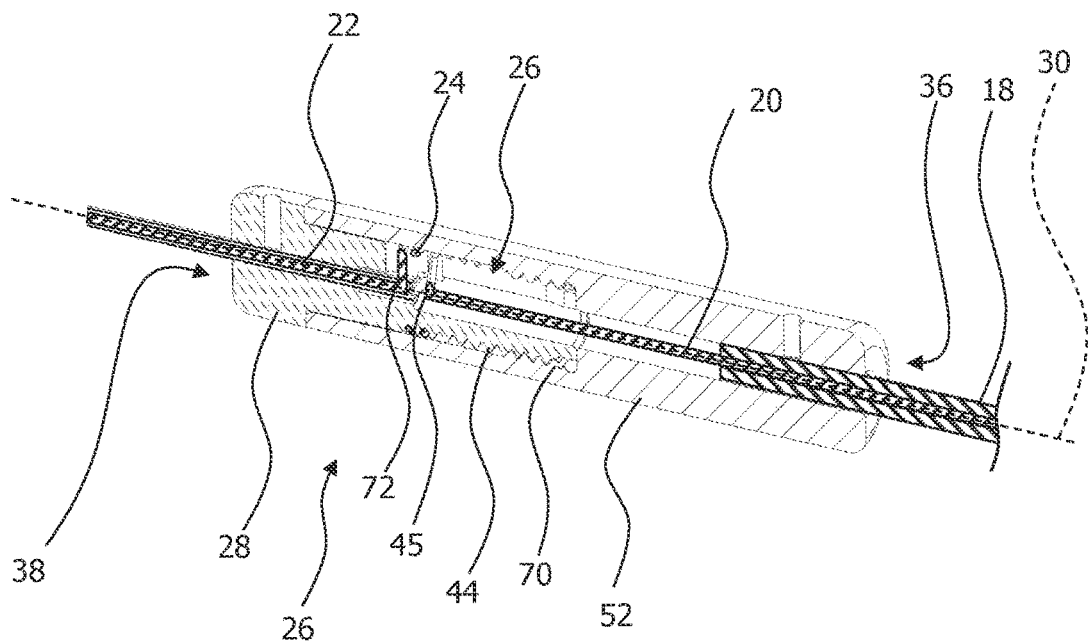
FIG. 5 shows a schematic perspective cross-sectional view of the strain relief unit.

In the following, reference is also made to FIG. 5, which shows a schematic perspective cross-sectional view of the strain relief unit 26. The core 28 is a one-piece structure. The core 28 is made of plastic. The core 28 is a hollow structure with a cylindrical basic shape. The first line section 20 extends into an interior of the core 28.

The strain relief unit 26 guides the line element 18 radially inwardly and radially outwardly with respect to the longitudinal axis 30. Specifically, with respect to the longitudinal axis 30 the first line section 20 is arranged at a first radial position, the second line section 22 is arranged at a second radial position, and the third line section 24 is arranged at a third radial position, wherein the first radial position and the second radial position are radially inward of the third radial position when viewed along the longitudinal axis 30.

In the present embodiment, the first line section 20 and the second line section 22 extend coaxially with respect to each other and coaxially with respect to the longitudinal axis 30. Hence, the first radial position and the second radial position are identical.

In other embodiments, all three radial positions may be different. Furthermore, in some embodiments the first line section 20 and/or the second line section 22 may extend coaxially with at least a portion of the third line section 24.

The line element 18 comprises a fourth line section 45 arranged between the first line section 20 and the third line section 24. The fourth line section 45 extends radially outward with respect to the longitudinal axis 30 when viewed along the longitudinal axis 30. Furthermore, the line element 18 comprises a fifth line section 72 arranged between the second line section 22 and the third line section 24. The fifth line section 72 extends radially outward with respect to the longitudinal axis 30 when viewed along the longitudinal axis 30.

When viewed perpendicular to the longitudinal axis, the line element 18 describes a double step within the strain relief unit 26, wherein coming from the first line section 20 the fourth line section 45 constitutes a step up from the first radial position to the third radial position, and the fifth line section 72 constitutes a step down from the third radial position to the second radial position.

The line element 18 may comprise a cable insulation, which may be at least partly removed and/or not present in any or all of the first through fifths line sections 20, 22, 24, 45, 72.

As can be seen in FIG. 4, at least one opening 47 is formed in the outer surface 32 of the core 28, wherein the line element 18 extends through the opening 47. The opening 47 comprises a slit 46, wherein the slit 46 is formed in the core 28, extends along the longitudinal axis 30 of the core 28 and overlaps the recess 36 in an overlap region 48. In the overlap region 48, each turn of the recess 34 around the core 28 is interrupted by the slit 46. The slit 46 connects the recess 36 to the interior of the core 28. The fourth line section 45 and the fifth line section 72 extend radially through the slit 46. Where it follows the recess 34, the third line section 24 extends across the slit 46 in the overlap region 48.

The third line section 24 is wound around the core 28 several times. A number of windings can be chosen as desired, for instance depending on an expected maximum strain.

The strain relief unit 26 further comprises a sleeve 52. The sleeve 52 comprises a cylindrical interior with an internal thread 70. The core 28 is threaded into the sleeve 52 and partly arranged within the sleeve 52. Specifically, the thread 44 of the core 28 is threaded into the internal thread 70 of the sleeve 52. Threading the core 28 into the sleeve 52 assures a connection between the two components which withstands large pulling forces. Furthermore, the strain relief unit 26 is easy to manufacture and easy to maintain, in particular since the strain relief unit 26 can be repeatedly opened and closed.

The sleeve 52 covers the recess 34. The sleeve 52 and the core 28 together form channels in which the third line section 24 extends, which channels are constituted by the recess and a portion of the sleeve 52 covering the recess 34. The sleeve 52 prevents the third line section 24 from jumping out of the recess in a radially outward direction.

The third line section 24 is arranged in a section of the thread 44 which is not threaded into the internal thread 70 of the sleeve 52. The third line section 24 is loose with respect to the core 28, i.e. it is not glued to the core 28 or otherwise stationary fixated, but can slide at least over a small distance. Thus, when a pulling force acts upon the first line section 20 with respect to the second line section 22, the third line section 24 may slightly move within the strain relief unit 26, wherein the pulling force is received by the recess 34, specifically by side walls defining the recess 34.

Figure 6:
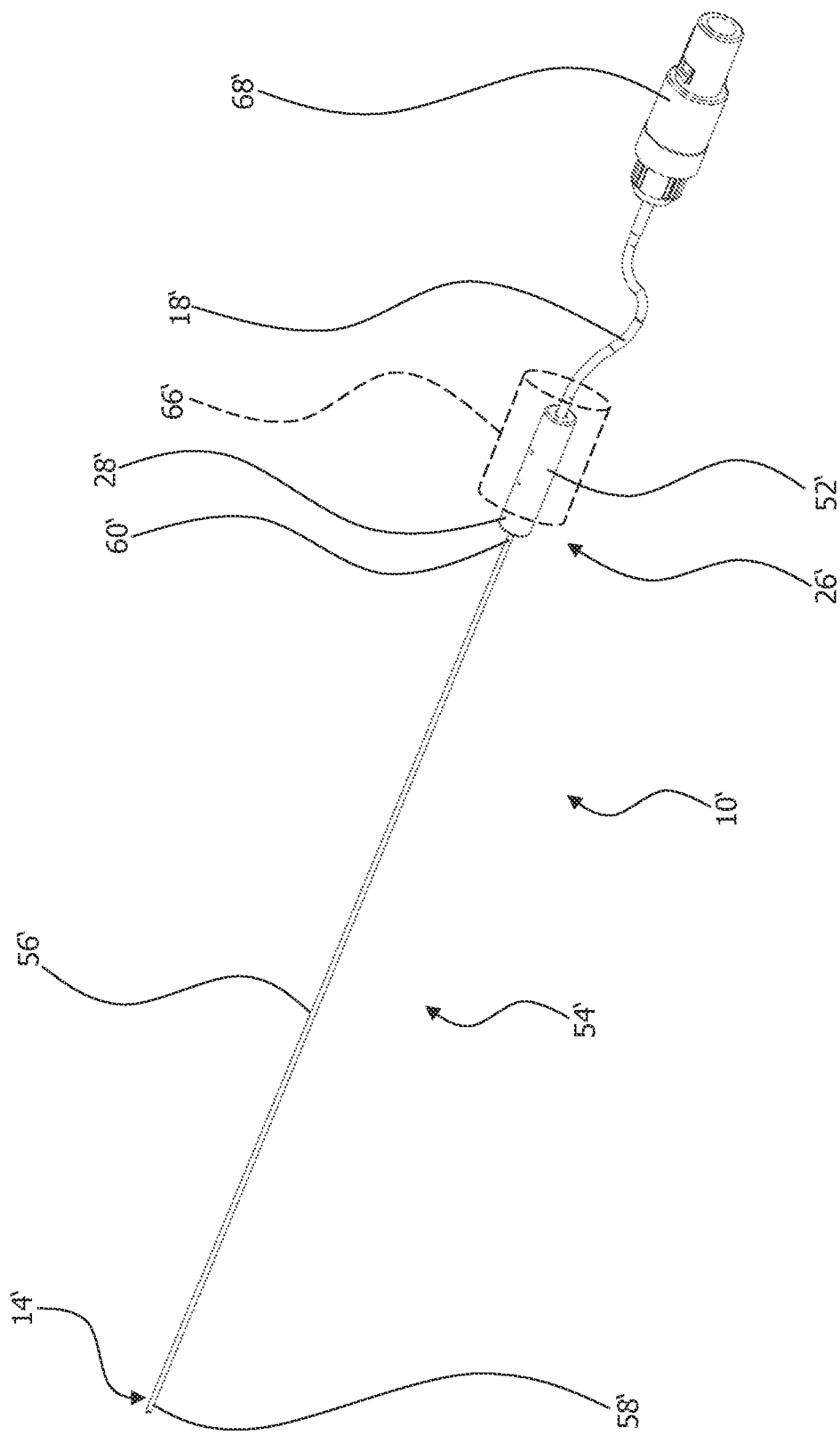
FIG. 6 shows a schematic perspective view of a surgical instrument with a tracking device according to a second embodiment.
Figure 7:
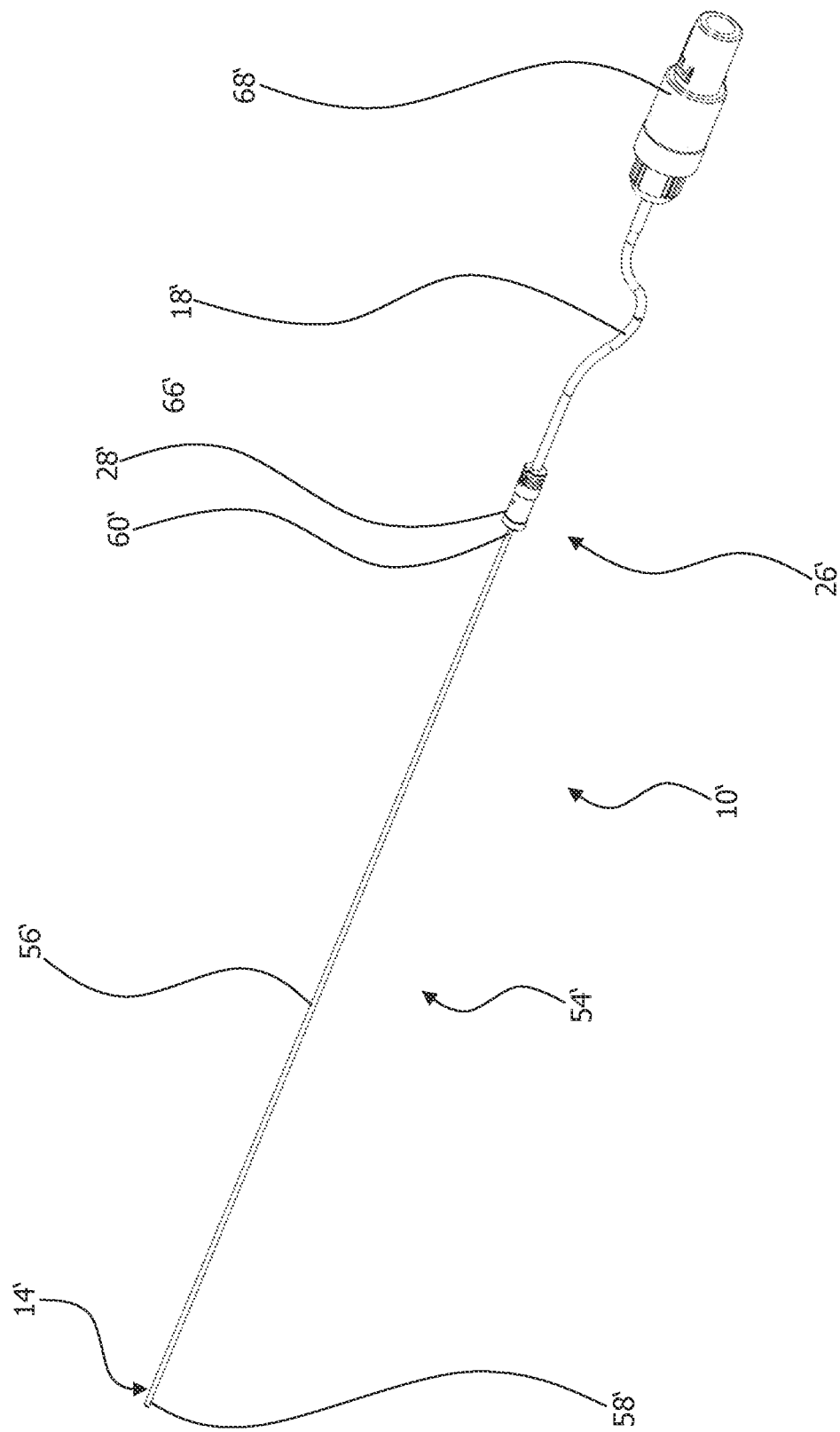
FIG. 7 shows a schematic perspective view of an interior of a part of the surgical instrument according to the second embodiment including a strain relief unit of the tracking device.

FIG. 6 shows a schematic perspective view of a surgical instrument 54' with a tracking device 10' according to a second embodiment. FIG. 7 shows a schematic perspective view of an interior of a part of the surgical instrument 54' according to the second embodiment which contains a strain relief unit 26' of the tracking device 10'. Reference signs used in the context of the second embodiment are denoted with an apostrophe. The same numbers are used to identify the same or similar objects. In the following, mostly the differences with respect to the previous embodiment will be described. Where an object shown in FIGS. 6 through 9 is not described, reference is made to the respective object as shown in the context of the previous embodiment.

The tracking device 10' comprises a strain relief unit 26' with a core 28' and a sleeve 52'. A line element 18' extends through the strain relief unit 26' and connects to an electromagnetic sensor 14' of the tracking device 10'. The strain relief unit 26' provides strain relief for the line element 18'

Figure 8:
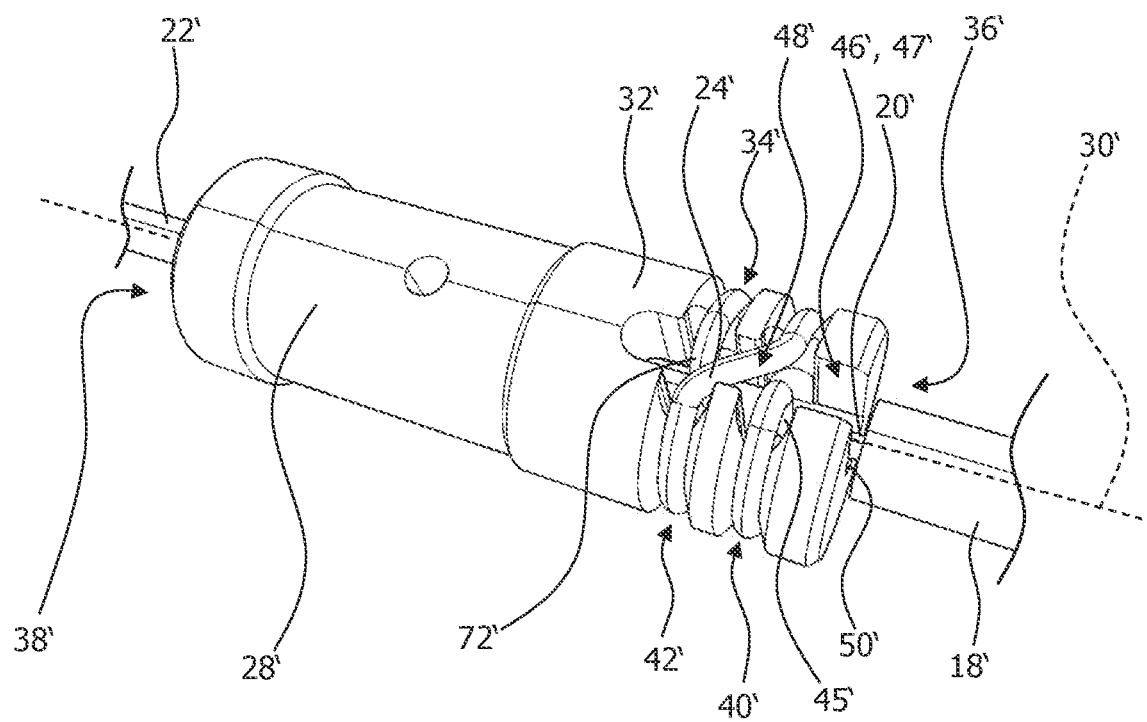
FIG. 8 shows a schematic perspective view of a core of the strain relief unit of the second embodiment.
Figure 9:
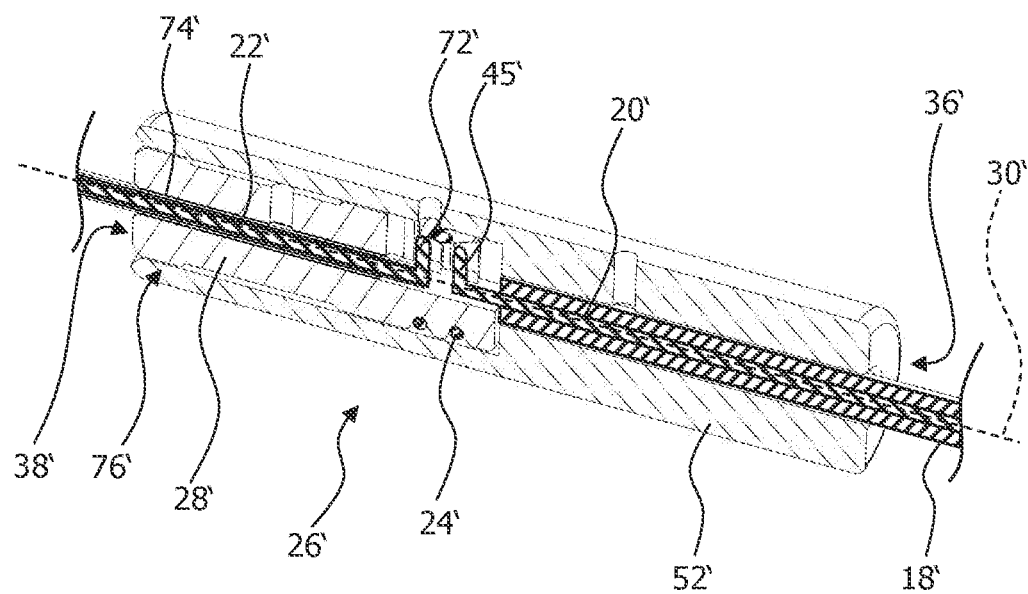
FIG. 9 shows a schematic perspective cross-sectional view of the strain relief unit of the second embodiment.

In the following, reference is made to FIGS. 8 and 9. FIG. 8 shows a schematic perspective view of the core 28' of the strain relief unit 26' of the second embodiment. FIG. 9 shows a schematic perspective cross-sectional view of the strain relief unit 26' of the second embodiment.

The core 28' has a longitudinal axis 30'. Similar to the previous embodiment, the line element 18' comprises a first line section 20' extending into the strain relief unit 26' on a proximal side and a second line section 22' extending into the strain relief unit 26' on a distal side. The first line section 20' and the second line section 22' extend at a first radial position and a second radial position, respectively, both coaxially with respect to the longitudinal axis 30'. A third line section 24' of the line element 18 is arranged between the first line section 20' and the second line section 22' at a third axial position that is radially outward of the first and second radial positions. A fourth line section 45' of the line element 18' connects the first line section 20' to the third line section 24' and extends radially outward with respect to the longitudinal axis 30'. A fifth line section 72' of the line element 18' connects the second line section 22' to the third line section 24' and extends radially outward with respect to the longitudinal axis 30'.

The core 28' comprises an outer surface 32' and at least one recess 34' which extends in the outer surface 32' circumferentially around the longitudinal axis 30', wherein the third line section 24' extends within the recess 34'. The core 28' comprises a cylindrical basic shape. The core 28' is a plastic one-piece component. The basic structure of the core 28' is a solid cylinder with different empty structures such as recesses, grooves, cavities etc. formed therein.

The recess 34' comprises two adjacent grooves 40', 42' that extend around the core 28' in a direction perpendicular to the longitudinal axis 30' of the core 28. The grooves 40', 42' are parallel ring grooves.

In other embodiments, a single groove may be used. Furthermore, in some embodiments a larger number of grooves may be chosen, such as three, four, five or even more. The number of grooves can be adjusted depending on an expected maximum strain.

A slit 46' is formed in the core 28' that extends along the longitudinal axis 30' and overlaps the two grooves 40, 42' in an overlap region 48'. The grooves 40', 42' are connected via the slit 46'. The third line section 24' extends along a first groove 40' of the grooves 40', 42', through the slit 46', and along a second groove 42' of the grooves 40', 42'.

The slit 46' comprises a base 50'. The first line section 20' extends at the base 50' of the slit 46'. The base 50' is located at a depth exceeding a radius of the core 28'. The base 50' is concave, such that the slit 46' has a U-shaped cross-section when viewed along the longitudinal axis 30'. The curvature of the base 50' and the depth of the slit 46' are chosen such that the first line section 20' extends coaxially with respect to the longitudinal axis 30'.

A channel 74' that extends coaxially with the longitudinal axis 30' is formed in the core 28'. The second line section 22' extends through the channel 74'. The channel may be connected to the slit 46', wherein a lower wall of the channel 74' may merge into the base 50' of the slit 46'.

As can be seen from FIG. 9, the sleeve 52 comprises a cylindrical receiving space 76' in which the core 28' is received. A diameter of the receiving space 76' essentially equals a diameter of the core 28'. The core 28' is arranged within the sleeve 52'.

The core 28' is glued to the sleeve 52'. In the shown embodiment, the core 28' is glued to the sleeve such that the line element 18' is not glued to the core 28' or to the sleeve 52'. For instance, the region of the core 28' comprising the recess 34' and the slit 46' may be free of glue. Gluing the core 28' and the sleeve 52' together allows for using a simple structure of the recess 34. Small inaccuracies regarding a rotational position of the sleeve 52' with respect to the core 28' do not affect the quality of the assembled strain relief unit 26'. Furthermore, the resulting structure is robust and withstands large pulling forces.

As is apparent form the previous description, the surgical instrument 54' of the second embodiment is generally of the same type as the surgical instrument 54 of the first embodiment. For both cases, the implementation with a stylet as surgical tool head 56, 56' is to be understood merely exemplarily. Various other types of surgical instruments are conceivable according to this disclosure.

In addition, the tracking devices 10, 10' may be implemented as tracking modules which can be connected to different types of surgical instruments. Such modules may for instance be implemented as screw-on caps, may click onto the respective surgical instrument, may be glued thereto or may otherwise be implemented to be permanently or removably attachable. In particular in this case an electromagnetic sensor may be located significantly closer to a strain relief unit as in the illustrated embodiments, for instance directly adjacent to a strain relief unit.

For both shown embodiments there may be a variant in which the line element 18, 18' and in particular the third line section 24, 24' is glued to the core 28, 28' and/or the sleeve 52, 52'.

The features described in relation to the exemplary embodiments shown in the drawings can be readily combined to result in different embodiments. It is apparent, therefore, that the present disclosure may be varied in many ways. Such variations are not to be regarded as a departure from the scope of the invention which is defined by the claims appended hereto.

The invention claimed is:

1. A tracking device for use in a surgical navigation system, the tracking device comprising:
    an electromagnetic sensor configured to generate a sensor signal that depends on an external electromagnetic field;
    at least one line element electrically connected to the electromagnetic sensor, wherein the line element comprises a first line section, a second line section, and a third line section arranged between the first line section and the second line section; and
    a strain relief unit comprising a core, wherein the core comprises a longitudinal axis, an outer surface and at least one recess which extends in the outer surface circumferentially around the longitudinal axis, wherein the first line section extends into the strain relief unit on a first side of the strain relief unit, the second line section extends into the strain relief unit on a second side of the strain relief unit, and the third line section follows a path defined by the recess.

2. The tracking device of claim 1, wherein the recess extends around the core several times.

3. The tracking device of claim 1, wherein the recess extends along a circle when viewed along the longitudinal axis.

4. The tracking device of claim 1, wherein the recess comprises at least two adjacent grooves that extend around the core in a direction substantially perpendicular to the longitudinal axis of the core.

5. The tracking device of claim 1, wherein the recess is part of a thread formed in the outer surface of the core.

6. The tracking device of claim 1, wherein the strain relief unit guides the line element in a guiding direction, wherein the guiding direction is at least one of radially inward direction and a radially outward direction with respect to the longitudinal axis.

7. The tracking device of claim 1, wherein, with respect to the longitudinal axis, the first line section is arranged at a first radial position and/or the second line section is arranged at a second radial position, and the third line section is arranged at a third radial position, wherein at least one of the first radial position and the second radial position is radially inward of the third radial position when viewed along the longitudinal axis.

8. The tracking device of claim 1, wherein the line element comprises at least one of a line section arranged between the first line section and the third line section and a line section arranged between the second line section and the third line section, wherein said line section extends radially outward with respect to the longitudinal axis when viewed along the longitudinal axis.

9. The tracking device of claim 1, wherein at least one opening is formed in the outer surface of the core, wherein the line element extends through the opening.

10. The tracking device of claim 9, wherein the at least one opening comprises at least one slit, wherein the slit is formed in the core, extends along the longitudinal axis of the core and overlaps the recess in an overlap region, wherein the at least one recess comprises one or more turns relative to the longitudinal axis, and wherein in the overlap region each turn of the recess around the core is interrupted by the slit.

11. The tracking device of claim 10, wherein the slit comprises a base, and wherein the first line section extends at the base of the slit.

12. The tracking device of claim 1, wherein the strain relief unit further comprises a sleeve, wherein the core is arranged at least partly inside the sleeve.

13. The tracking device of claim 12, wherein the core is threaded into the sleeve.

14. The tracking device of claim 12, wherein the core is glued to the sleeve such that the line element is not glued to at least one of the core and the sleeve.

15. The tracking device of claim 1, wherein the core comprises a cylindrical basic shape.

16. The tracking device of claim 1, wherein the core is a one-piece unit.

17. A surgical instrument comprising:
a tracking device comprising:
an electromagnetic sensor configured to generate a sensor signal that depends on an external electromagnetic field;
at least one line element electrically connected to the electromagnetic sensor, wherein the line element comprises a first line section, a second line section, and a third line section arranged between the first line section and the second line section; and
a strain relief unit comprising a core, wherein the core comprises a longitudinal axis, an outer surface and at least one recess which extends in the outer surface circumferentially around the longitudinal axis, wherein the first line section extends into the strain relief unit on a first side of the strain relief unit, the second line section extends into the strain relief unit on a second side of the strain relief unit, and the third line section follows a path defined by the recess.

18. The surgical instrument of claim 17, further comprising a surgical tool head with a first end and a second end, wherein the electromagnetic sensor is arranged at the first end, the strain relief unit is arranged at the second end, and the line element extends along the surgical tool head.

19. The surgical instrument of claim 18, wherein the surgical tool head is a stylet.

20. A surgical navigation system for tracking a position of a surgical instrument, the surgical navigation system comprising:
a tracking device comprising:
an electromagnetic sensor configured to generate a sensor signal that depends on an external electromagnetic field;
at least one line element electrically connected to the electromagnetic sensor, wherein the line element comprises a first line section, a second line section, and a third line section arranged between the first line section and the second line section;
a strain relief unit comprising a core, wherein the core comprises a longitudinal axis, an outer surface and at least one recess which extends in the outer surface circumferentially around the longitudinal axis, wherein the first line section extends into the strain relief unit on a first side of the strain relief unit, the second line section extends into the strain relief unit on a second side of the strain relief unit, and the third line section follows a path defined by the recess;
a field generator for generating the external electromagnetic field; and
a localizer connected to the electromagnetic sensor of the tracking device of the surgical instrument for determining a position of the surgical instrument based on the sensor signal received from the electromagnetic sensor.

* * * * *